US008545521B2

(12) United States Patent
McClurg et al.

(10) Patent No.: US 8,545,521 B2
(45) Date of Patent: *Oct. 1, 2013

(54) SUTURING SYSTEM AND ASSEMBLY

(75) Inventors: Steven McClurg, Roseville, MN (US); Christopher Anthony Thierfelder, Minneapolis, MN (US); Allen Gaynor, Coon Rapids, MN (US); Pornpimon Narthasilpa, St. Paul, MN (US); Timothy Andrew Bachman, St. Paul, MN (US); Christian Richard Trifilio, St. Paul, MN (US); Matthew Vail Leyden, St. Paul, MN (US); Nicholas Ellering, Crystal, MN (US); Michael K. Luk, Hopkins, MN (US); James Leigh Lindenberg, Wyoming, MN (US); Donald Wolf, Vadnais Heights, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/591,235

(22) Filed: Aug. 22, 2012

(65) Prior Publication Data
US 2012/0323263 A1 Dec. 20, 2012

Related U.S. Application Data

(63) Continuation of application No. 12/833,006, filed on Jul. 9, 2010, now Pat. No. 8,282,657, and a continuation of application No. 12/545,905, filed on Aug. 24, 2009.

(30) Foreign Application Priority Data

Jul. 22, 2009 (DK) .................................. 2009 70073
Jul. 22, 2010 (WO) ................ PCT/DK2010/050195

(51) Int. Cl.
*A61B 17/04* (2006.01)

(52) U.S. Cl.
USPC ............ 606/145; 606/139; 606/144; 606/148

(58) Field of Classification Search
USPC ............................ 606/139, 144, 145, 147, 18
See application file for complete search history.

(56) References Cited

U.S. PATENT DOCUMENTS 5,364,407 A 11/1994 Poll
5,792,153 A 8/1998 Swain et al.
(Continued)

OTHER PUBLICATIONS

Office Action mailed on Apr. 25, 3013 in U.S. Appl. No. 13/414,738.

*Primary Examiner* — Corrine M McDermott
*Assistant Examiner* — Alexander Orkin
(74) *Attorney, Agent, or Firm* — Coloplast Corp., Coloplast A/S; Nick Baumann

(57) ABSTRACT

A suturing assembly is provided that is configured to pull a capsule attached to a suture through tissue. The suturing assembly includes a shaft aligned on a longitudinal axis of the suturing assembly, and a head coupled to the shaft. The head includes a proximal portion and a distal end spaced apart from the proximal portion by a throat. The proximal portion houses a needle that is movable through a needle exit port. The proximal portion of the head and the needle exit port are both aligned on the longitudinal axis. A proximal side of the distal end of the head defines a cavity adapted to receive the capsule and a distal side of the distal end of the head defines a slot adapted to allow the suture to pass through the distal end of the head and into the cavity.

10 Claims, 16 Drawing Sheets

(56) References Cited

U.S. PATENT DOCUMENTS

| | | | |
|---|---|---|---|
| 5,931,844 A | 8/1999 | Thompson et al. | |
| 6,554,845 B1* | 4/2003 | Fleenor et al. | 606/148 |
| 7,090,690 B2 | 8/2006 | Foerster et al. | |
| 8,282,657 B2* | 10/2012 | McClurg et al. | 606/145 |
| 2002/0143234 A1 | 10/2002 | LoVuolo | |
| 2002/0193810 A1* | 12/2002 | Hill et al. | 606/144 |
| 2003/0149447 A1 | 8/2003 | Morency et al. | |
| 2003/0233108 A1* | 12/2003 | Gellman et al. | 606/144 |
| 2004/0097968 A1 | 5/2004 | Shikhman et al. | |
| 2004/0186340 A1 | 9/2004 | Reed et al. | |
| 2005/0033319 A1 | 2/2005 | Gambale et al. | |
| 2005/0154403 A1* | 7/2005 | Sauer et al. | 606/139 |
| 2008/0045976 A1 | 2/2008 | Gibbons, Jr. et al. | |
| 2011/0118758 A1 | 5/2011 | Sauer | |
| 2011/0270280 A1 | 11/2011 | Saliman | |
| 2012/0316582 A1 | 12/2012 | Nobles et al. | |

\* cited by examiner

SUTURING SYSTEM AND ASSEMBLY

This application is a continuation application of U.S. Ser. No. 12/833006, filed on Jul. 9, 2010, now U.S. Pat. No. 8,282,657, U.S. Ser. No. 12/545,905, filed on Aug. 24, 2009, and claims the benefit of priority from the prior Denmark Patent Application No. 2009 70073, filed Jul. 22, 2009 and PCT/DK/2010/050195 filed Jul. 22, 2010, the entire contents of each of which are incorporated herein by reference.

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon digitally palpates a desired location for placement of the suture and is unable to see the suture site.

Improved suturing instruments and improved methods of delivering sutures would be welcomed by the surgical staff.

SUMMARY

One aspect provides a suturing assembly configured to place suture in tissue. The suturing assembly includes a handle having an actuator, a shaft coupled to the handle, and a head coupled to the shaft. The head includes a proximal portion housing a needle movable through a needle exit port and a distal end spaced apart from the proximal portion by a throat, the distal end defining a cavity. The actuator is configured to move the needle out of the needle exit port formed in the proximal portion of the head and across the throat to engage a capsule disposed in the cavity formed in the distal end of the head, where the capsule is attached to the suture.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
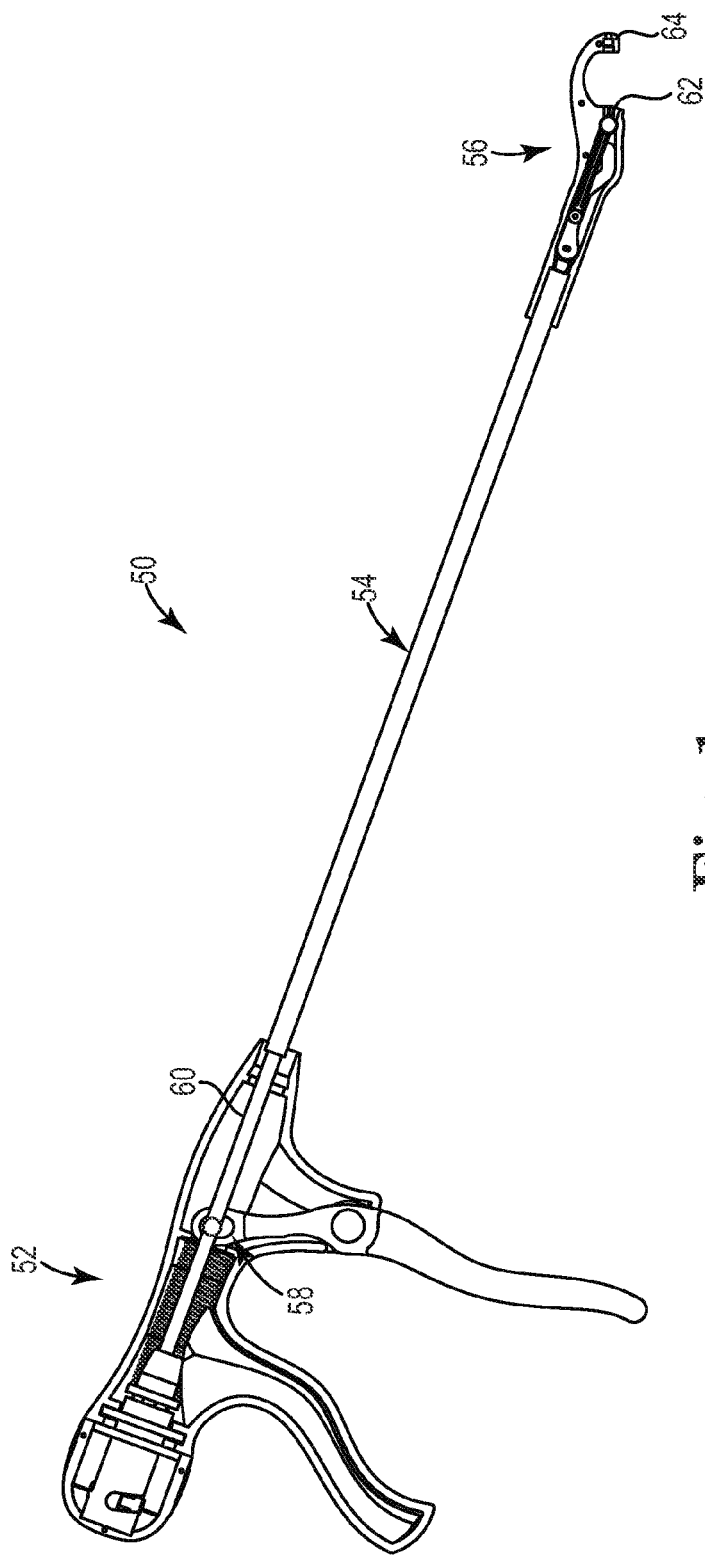
FIG. 1 is a side plan view of a suturing instrument according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification, shunt means to move an object away from a first axis to another axis that is different from the first axis. For example, in one embodiment a suturing device includes a needle that is moved in a first direction (e.g., along a longitudinal axis) and is subsequently moved in a second direction different from the first direction (i.e., away from the longitudinal axis); thus the needle is shunted away from a longitudinal axis when deployed from the device.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

Embodiments provide a suturing assembly having a needle housed in a proximal end portion of a head of the assembly, where the needle is deployed longitudinally out of the proximal end portion of the head through a mass of tissue and subsequently grasps a suture assembly. The needle retracts after engaging the suture assembly and pulls the suture assembly through the needle-hole (e.g., lesion) formed in the tissue. In this manner, the suturing assembly reaches through the tissue, grasps the suture assembly, and retracts the suture assembly through the tissue to complete a "stitch" in the tissue.

In one embodiment, a suture system is provided that includes the suture assembly and a capsule that is attached to a length of suture. Embodiments of the suturing assembly include a head having a distal end that defines a cavity sized to retain the capsule. A needle is housed within a proximal end portion of the head and is movable from a needle exit port into the cavity formed in the distal end of the head. The needle is configured to engage the capsule of the suture assembly.

Embodiments provide a suturing assembly having a linear head that is configured to throw a needle longitudinally out of a needle exit port, across a throat space, and into a cavity formed in a distal end of the linear head.

Embodiments provide a suturing assembly having a head with a radially offset distal end, where the head is configured to throw a needle longitudinally in a first direction through a needle exit port, shunt the needle away from the longitudinal axis in a second direction different from the first direction, and into the cavity formed in the radially offset distal end.

Embodiments provide a suturing assembly configured to throw a needle into frictional engagement with a capsule towing a length of suture. The suturing assembly places a stitch in the tissue each time the capsule is retrieved, and the surgeon, upon seeing the retrieved capsule, is provided with positive visual feedback of the successful application of the suture.

FIG. 1 is a side plan view of a suturing assembly 50 configured to place suture in tissue according to one embodiment. Suturing assembly 50 includes a handle 52, a shaft 54 coupled to handle 52, and a head 56 coupled to shaft 54. Handle 52 thus defines a proximal end of suturing assembly 50 and is nearest a user of suturing assembly 50.

In one embodiment, handle 52 includes an actuator 58 communicating with a rod 60 that is disposed within shaft 54. When actuator 58 is activated, rod 60 moves through shaft 54 to extend a needle 62 stored within a proximal end portion of head 56 axially outward through tissue and toward a distal end 64 of head 56. Thus, needle 62 moves away from the user (who is holding handle 52 at the proximal end of suturing assembly 50) toward distal end 64 of suturing assembly 50.

In one embodiment, a capsule (not shown) is retained within distal end 64, and needle 62 is shaped to frictionally engage and mate with the capsule, remove the capsule from distal end 64, and retract the capsule into the proximal end portion of head 56. In this manner, the suture towed behind the capsule is "thrown" through the tissue. Embodiments described below include a guide pin located within head 56 that is configured to disengage the capsule from needle 62.

Suturing assembly 50 is suited for the intracorporeal suturing of tissue during surgery, and in one embodiment is provided as a sterile disposable surgical instrument that is discarded after the surgical procedure. To this end, the components of assembly 50 are selected to be compatible with gas, steam, or radiation sterilization.

Figure 2:
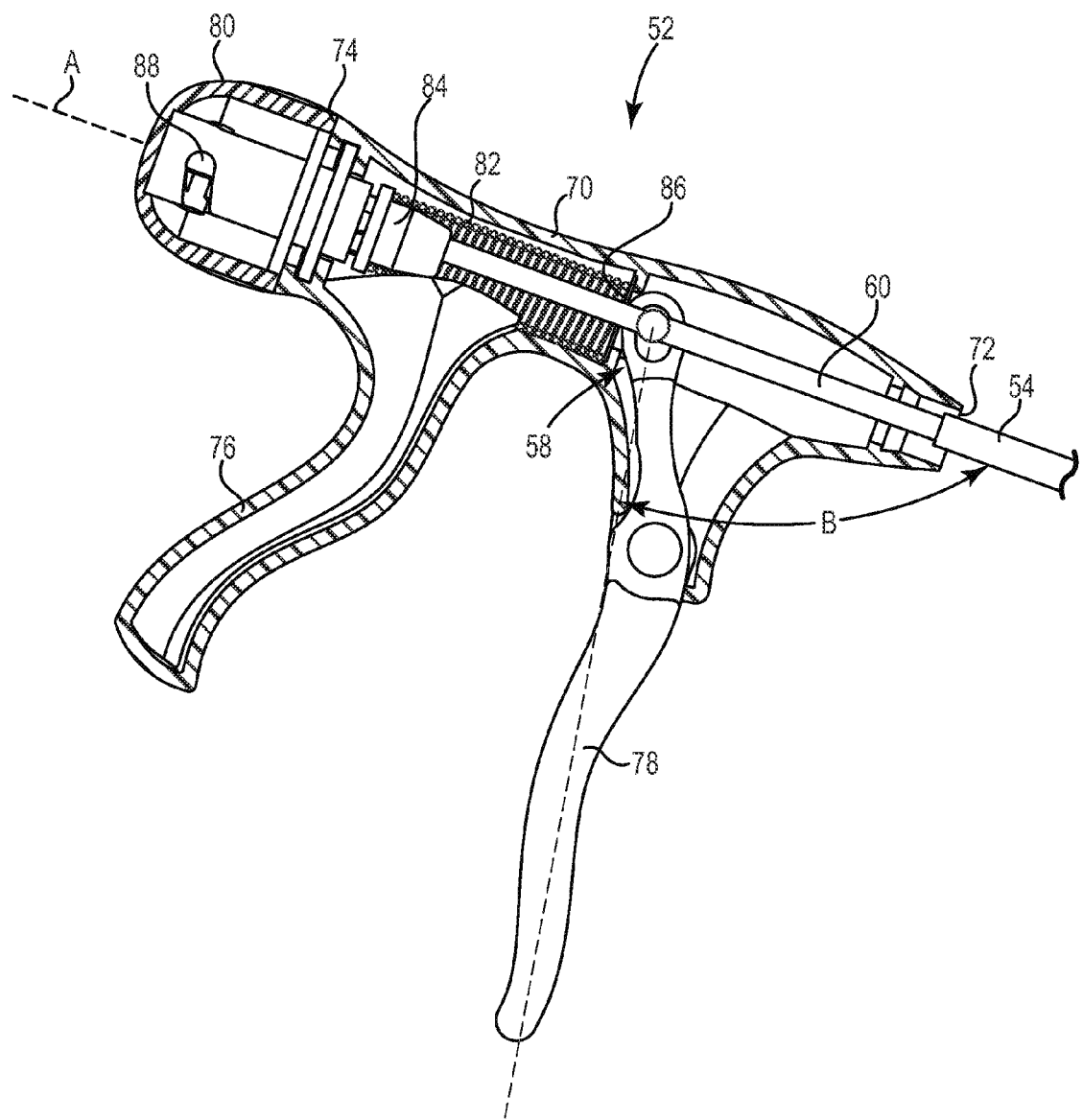
FIG. 2 is a cross-sectional view of one embodiment of a handle of the suturing instrument illustrated in FIG. 1.

FIG. 2 is a cross-sectional view of one embodiment of a handle 52. In one embodiment, handle 52 is aligned with a major longitudinal axis A and includes a body 70 extending between a distal end 72 and a proximal end 74, a thumb brace 76 extending laterally from body 70, a trigger 78 spaced apart from thumb brace 76, and a knob 80 coupled to proximal end 74.

In one embodiment, body 70 is fabricated from plastic, for example via injection molding. Suitable plastic materials for the fabrication of body 70, brace 76, and knob 80 include, as examples, polycarbonate, polyethylene, acrylonitrile butadiene styrene, acrylic, or nylon. In one embodiment, brace 76 is integrally molded with a clamshell-style of body 70 and these two components are joined together to retain trigger 78 and knob 80. Trigger 78 is formed to have sufficient strength to resist bending when activated by the human hand. Suitable materials for forming trigger 78 include metal such as aluminum or plastics such as polyetherimide or poly-ether-ether-ketone.

Shaft 54 is coupled to distal end 72 of body 70, and rod 60 is disposed within shaft 54 and coupled to trigger 78. In one embodiment, actuator 58 includes trigger 78 attached to rod 60 and a spring 82 disposed within a spring pusher 84 and biased against and an internal rib 86. Trigger 78 is movable toward thumb brace 76 to move rod 60 in a distal direction longitudinally within shaft 54, which compresses spring 82. When trigger 78 is released, spring 82 extends to push spring pusher 84 proximally, which retracts or returns rod 60 toward proximal end 74. Trigger is spaced apart from thumb brace 76 by a distance of approximately 4-12 cm to enable the fingers of the user to comfortably activate trigger 78. Trigger 78 is disposed at an angle B relative to the longitudinal axis A of body 70, and in an exemplary embodiment the angle B is between 70-110 degrees such that trigger 78 is approximately orthogonal to longitudinal axis A.

Actuator 58 is configured to move rod 60 forward in a distal direction and rearward in a proximal direction within shaft 54. In one embodiment, it is desirable to move rod 60 rearward an additional distance to disengage the suture assembly described below from needle 62 (FIG. 1). To facilitate this, rod 60 includes an insert (not shown) that communicates through spring pusher 84 and is captured in window 88. When knob 80 is turned, spring pusher 84 turns and the insert attached to rod 60 is retracted back in a proximal direction due to the angle of window 88, which retracts rod 60 an additional distance into body 70. For example, in one embodiment knob 80 is configured such that a 180 degree clockwise of knob 80 relative to end 74 draws rod 60 an additional distance of about 2 mm into body 70. Although knob 80 is configured to retract rod 60 further into body 70 via a turning motion, other mechanisms such as levers or draw bars for retracting rod 60 incrementally rearward are also acceptable.

Figure 3:
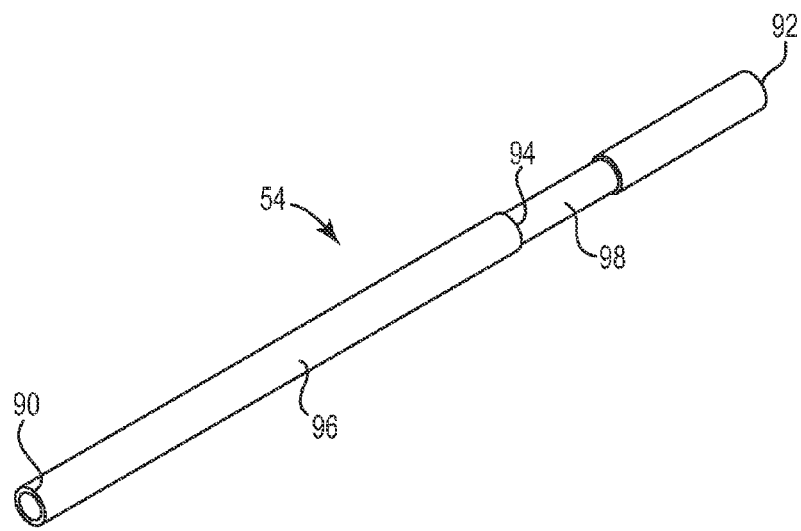
FIG. 3 is a side view of one embodiment of a shaft of the suturing instrument illustrated in FIG. 1.

FIG. 3 is a side view of shaft 54. One suitable embodiment of shaft 54 includes a substantially rigid aluminum annular tube extending between a proximal end that is attachable to handle 52 (FIG. 1) and a distal end that is attachable to head 56. Other substantially rigid materials, such as stainless steel, are also suitable selections for fabricating shaft 54. Another embodiment of shaft 54 includes a distal end portion associated with distal end 92 that is flexible and configured to bend laterally relative to first section 96 to enable the surgeon to selectively direct head 56 to a desired location.

For example, one embodiment of shaft 54 includes a proximal end 90 that is attachable to handle 52 (FIG. 1), a distal end 92 that is attachable to head 56 (FIG. 1), and a crimp 94 or a weld 94 connects a first section 96 to a second section 98. In one embodiment, shaft 54 is formed as a thin-walled tube with first section 96 formed of a first material and a second section 98 is formed of a different second material. In an exemplary embodiment, first section 96 is formed of 6,000 series aluminum and a second section 98 is formed of 3000 series aluminum, with these two metal sections 96, 98 joined together by crimp/weld 94. The 6000 series aluminum is selected to have a shear modulus of a sufficient value to preclude the user from bending first section 96 as instrument 50 is manipulated. For example, in one embodiment the shear modulus of first section 96 is approximately 30 $GN/m^2$. The 3000 series aluminum is selected to have a shear modulus of a sufficient value to enable a user to bend the second section 98 with their hands, which enables the user to shape and guide second section 98 (which is attached to head 56) in controlling and guiding the placement of sutures with head 56. For example, in one embodiment the shear modulus of second section 98 is approximately 10 $GN/m^2$. In another example, in one embodiment the yield strength of first section 96 is approximately 30 $GN/m^2$. The 3000 series aluminum is selected to have a yield strength of a sufficient value to enable a user to bend the second section 98 with their hands, which enables the user to shape and guide second section 98 (which is attached to head 56) in controlling and guiding the placement of sutures with head 56. For example, in one embodiment the yield strength of second section 98 is approximately 10 $GN/m^2$.

One example of suitable lengths for sections 96, 98 is for first section 96 to have a length between 4-24 cm and second section 98 to have a length between 1-10 cm. Other lengths for sections 96, 98 are also acceptable. In one embodiment, crimp/weld 94 is provided as a metal peripheral crimp securing first section 96 to second section 98.

Figure 4:
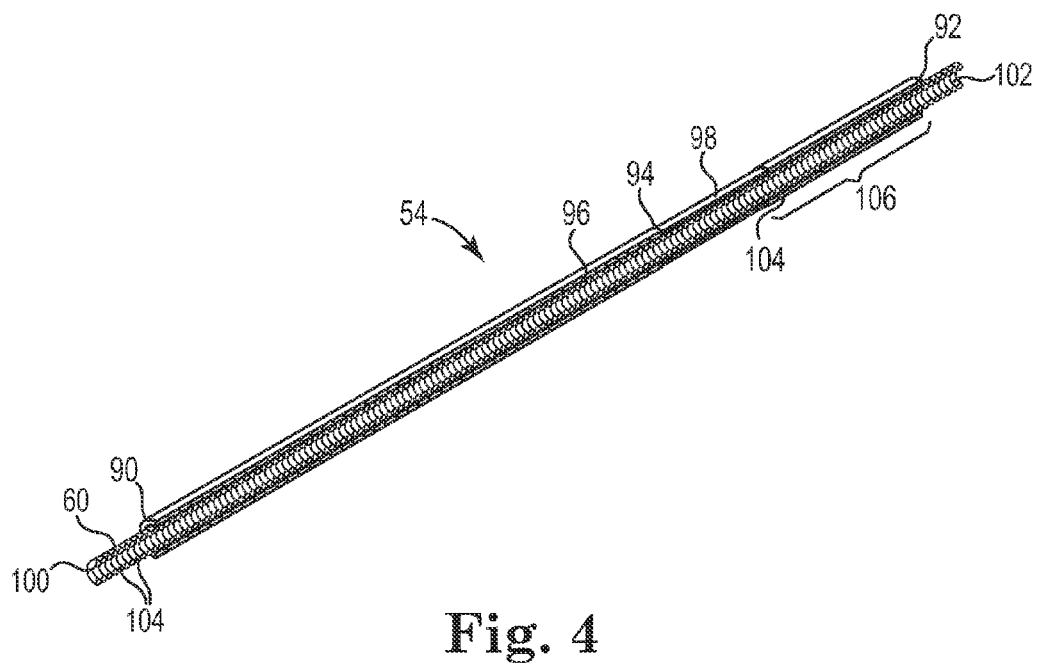
FIG. 4 is a cross-sectional view of one embodiment of a push rod disposed within the shaft illustrated in FIG. 3.

FIG. 4 is a cross-sectional view of rod 60 disposed within shaft 54. Rod 60 generally includes a proximal end 100 that couples with push rod 84 (FIG. 2) and a distal end 102 that communicates with needle 62. In one embodiment, proximal end 100 of rod 60 is rigid and the remaining portion of rod 60 is formed to include a coiled spring, where multiple coils 104 abut such that rod 60 has sufficient column strength (e.g., along its major axis) to enable rod 60 to activate needle 62 and is provided with flexibility to bend laterally. In one embodiment, an entire length of rod 60 is formed of a coiled stainless steel spring and is constrained within shaft 54 (FIG. 3) to provide rod 60 with a column strength configured to resist buckling under axial loads, and the coils 104 are configured to enable head 56 (FIG. 1) to flex and move laterally under the application of a radial load. In this manner, the user of instrument 50 (FIG. 1) can bear down on shaft 54 and rod 60 to apply a forward-applied force, while also having the flexibility and control of shaping where head 56 is oriented relative to handle 52.

In one embodiment, rod 60 is formed of a coiled stainless steel spring and includes a polyethylene jacket, as one example, disposed around the coiled spring.

In one embodiment, only a leading section 106 of rod 60 is formed of coiled springs 104, where leading section 106 corresponds to the flexible second section 98 of shaft 54, such that rod 60 is provided with substantially the same lateral flexibility as shaft 54.

In one embodiment, rod 60 is formed of aluminum and configured to have similar flexibility as shaft 54.

Figure 5:
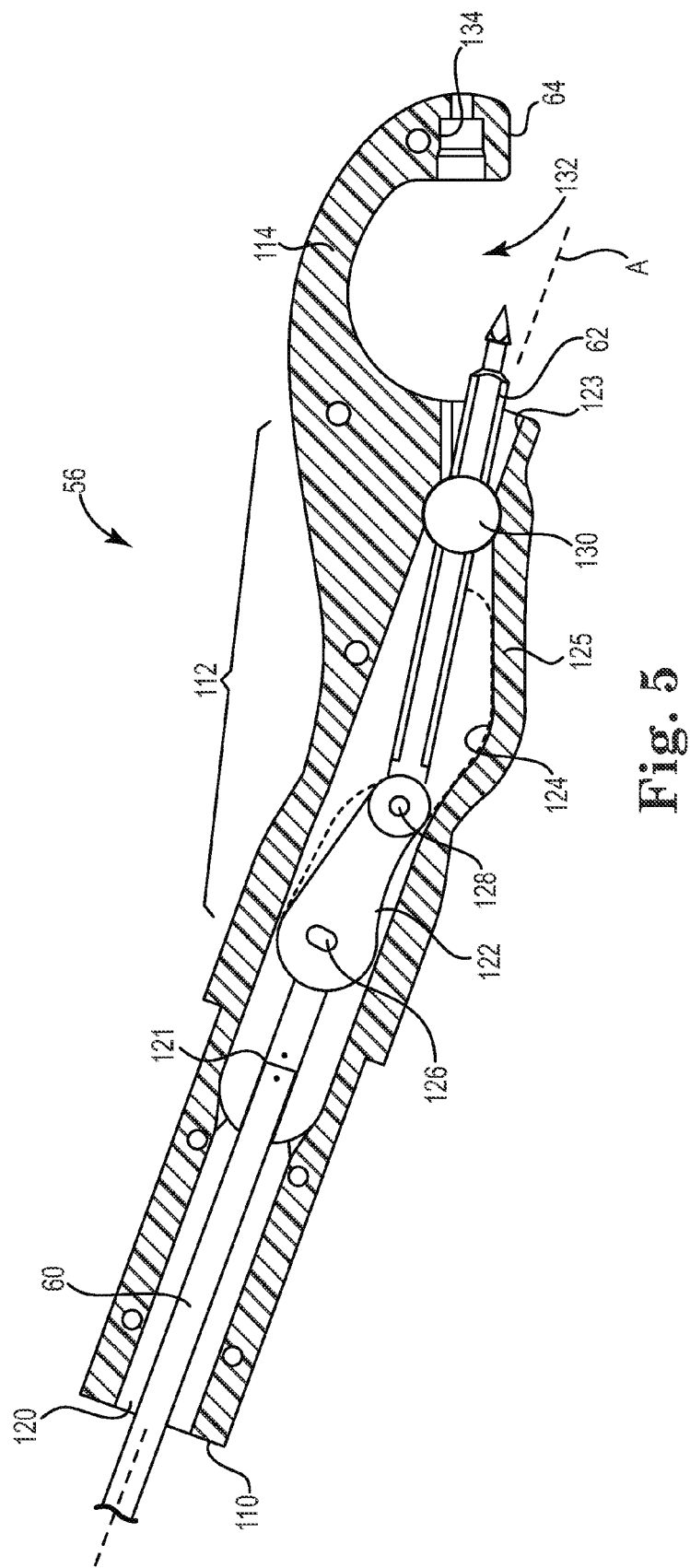
FIG. 5 is a cross-sectional view of a head of the suturing instrument illustrated in FIG. 1 including a movable needle according to one embodiment.

FIG. 5 is a cross-sectional view of head 56. In one embodiment, head 56 is formed of two mating clamshell components, and the view of FIG. 5 is taken with one half of the clamshell structure removed so that the internal features of head 56 are visible. Head 56 is molded from plastic, for example from a polyether imide plastic sold under the trademark Ultem, or from glass-filled polyether imide plastics also sold under the trademark Ultem.

In one embodiment, head 56 includes a proximal end 110 opposite distal end 64, a proximal end portion 112 extending from proximal end 110, and a neck 114 that extends between proximal end portion 112 and distal end 64. Head 56 is attachable to shaft 54, and in one embodiment includes an opening 120 sized to receive shaft 54 such that rod 60 extends into proximal end portion 112 and couples with a link 122 that is attached to needle 62. In one embodiment, distal end 64 is not aligned with, but is rather offset radially from longitudinal axis A, to more comfortably position shaft 54 for manipulation by the surgeon as head 56 is engaged with tissue.

In one embodiment, a clevis pin 121 connects a proximal end of link 122 to rod 60 and a distal end of link 122 is coupled to needle 62. Movement of rod 60 moves link 122, which moves needle 62 into and out of a needle exit port 123 formed in proximal end portion 112. In one embodiment, a trace 124 that is formed on an interior surface 125 of proximal end portion 112 of head 56, and link 122 is configured to translate and rotate within trace 124 to translate needle 62 along axis A and pitch needle up/down relative to axis A. For example, in one embodiment link 122 includes a first pin 126 that couples with clevis 121 and a second pin 128 that couples with needle 62. Axial movement of rod 60 translates to axial movement of link 122 and needle 62, and link 122 rotates about pins 126, 128 to shunt a path of needle 62 off of axis A.

Link 122 is thus configured to translate within trace 124 to move needle 62 in/out relative to needle exit port 123, and rotate relative to pins 126, 128 to direct movement of needle 62 up/down relative to longitudinal axis A. In one embodiment proximal end portion 112 includes a guide pin 130 that defines a bore sized to receive needle 62. Needle 62 is configured to slide through the bore formed in guide pin 130, and guide pin 130 is rotatable to allow needle 62 to pitch relative to longitudinal axis A as needle 62 moves axially, for example as needle 62 moves into engagement with distal end 64.

Neck 114 extends between proximal end portion 112 and distal end 64 and defines a throat 132. Needle 62 is movable from proximal end portion 112, out of needle exit port 123, across throat 132, and into a cavity 134 formed in distal end 64. In one embodiment, distal end 64 and cavity 134 are both radially spaced away from longitudinal axis A, and guide pin 130 rotates to enable needle 62 to move out of the needle exit port 123, pitch upwards, and into cavity 134. In one embodiment, a top surface of neck 114 defines an open, exposed groove configured to receive and guide suture that extends from the capsule 152 (FIG. 6) captured in cavity 134 back to handle 52 (FIG. 1).

As described below, cavity 134 is configured to retain a capsule attached to suture (see FIG. 7), and needle 62 is configured to penetrate tissue and enter cavity 134, engage the capsule, and pull the capsule through the tissue and into needle exit port 123 to "throw" the suture across throat 132. As described below, embodiments of head 56 include mechanisms configured to linearly direct needle 62 out of needle exit port 123 across throat 132 and into cavity 134 for engagement with the capsule. Other embodiments of head 56 include mechanisms configured to shunt needle 62 (e.g., pitch needle 62 upward relative to axis A away from needle exit port 123 and into cavity 134 for engagement with the capsule).

Figure 6:
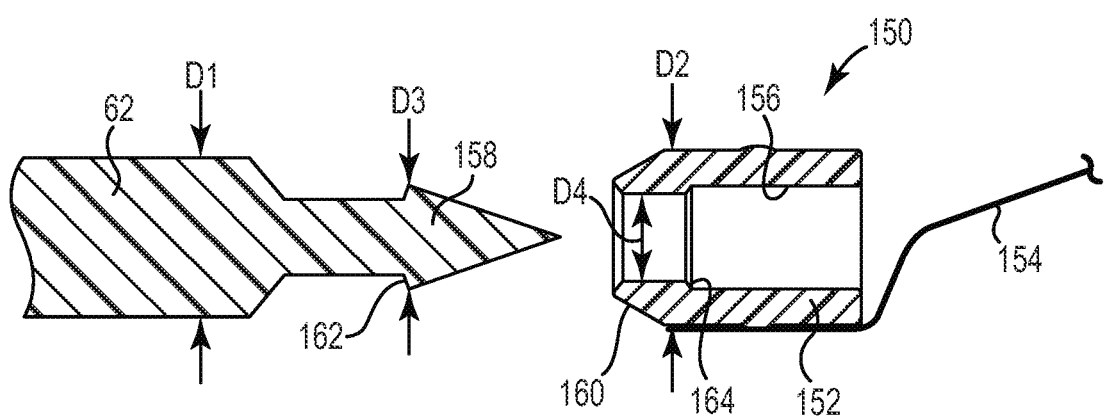
FIG. 6 is a cross-sectional view of a suture assembly including suture attached to a capsule that is configured to couple with a needle of the suturing instrument illustrated in FIG. 1 according to one embodiment.

FIG. 6 is a side view of needle 62 aligned for engagement with a suture assembly 150 according to one embodiment. Needle 62 is preferably machined from metal such as stainless steel or a shape memory alloy such as NITINOL (Nickel Titanium Naval Ordinance Laboratory), as examples. Suture assembly 150 includes a capsule 152 and suture 154 extending from capsule 152. In one embodiment, capsule 152 is molded from plastic to integrally capture suture 154. Suitable plastic materials for fabricating capsule 152 include polypropylene, polysulfone, urethane, or polyetherimide as examples. Suture 154 includes monofilament suture, braided suture, coated suture materials or the like, as examples.

Capsule 152 is sized to be deposited and retained in cavity 134 (FIG. 5) and defines a recess 156 configured to receive a leading end 158 of needle 62. In one embodiment, needle 62 is shaped to promote secure engagement with capsule 152 and leading end 158 is formed to have a conical point with a shoulder 162 that is sized to be pressed into engagement with a flange 164 of recess 156. For example, flange 164 that is shaped and sized to frictionally engage (e.g., snap-fit) in a "locked" manner with a shoulder 162 of needle 62 as needle 62 is driven into recess 156. Capsule 152 is configured to be detached from needle 62 by guide pin 130 (FIG. 5) after needle 62 pulls capsule 152 rearward in a proximal direction into head 56.

The conical point of needle 62 is configured to form a channel when advanced through tissue, and capsule 152 is sized to be pulled through the channel in the tissue made by needle 62. In one embodiment, leading end 160 of capsule 152 is chamfered and needle 62 is configured to draw the chamfered (or truncated) end 160 of capsule 152 first through the tissue. In one embodiment, leading end 160 of capsule 152 is a blunt end similar to that illustrated for the trailing end of the capsule 152, and needle 62 is configured to draw the blunt end 160 of capsule 152 blunt end-first through the tissue.

For example, in one embodiment needle 62 has a first diameter D1 and capsule 152 has a diameter D2, were diameter D1 is equal to or greater than diameter D2. In this manner, capsule 152 is sized to follow needle 62 and be retracted through the channel formed in the tissue by needle 62.

Leading end 158 of needle 62 is sized to frictionally engage with recess 156 formed in capsule 152. For example, in one embodiment leading end 158 has a diameter D3 that is slightly greater than a diameter D4 formed in an opening of recess 156. In this manner, when leading end 158 of needle 62 is inserted into recess 156, leading end 158 is forced into and seats within and captures capsule 152.

FIGS. 7A-7F are schematic cross-sectional views illustrating a suturing system 166 including suturing device 50 and suture assembly 150 employed to throw needle 62 from a proximal location to a distal location of head 56, engage needle 62 with a capsule 152/suture 154 of assembly 150, and retract capsule 152/suture 154 through tissue.

Figure 7A:
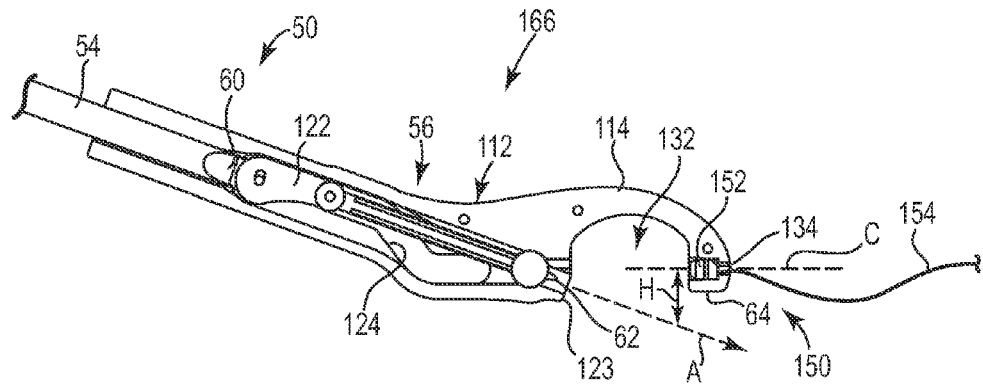
FIG. 7A is a schematic cross-sectional view of the head of the suturing instrument illustrated in FIG. 5 with the needle retracted within the head according to one embodiment.

FIG. 7A is a schematic cross-sectional view of system 166 with needle 62 fully retracted within needle exit port 123 of proximal end portion 112 of head 56. Capsule 152 is seated in cavity 134 with suture 154 trailing distal of head 56. In one embodiment, it is recommended that the surgeon direct a trailing end of suture 154 over distal end 64 of head 56 and back toward a proximal end of shaft 54 for ease of managing suture assembly 150 during the procedure. For example, one embodiment of distal end 64 includes a slot configured to enable the suture 154 to pass through distal end 64 to facilitate loading capsule 152 into cavity 134. In one embodiment, rod 60 and needle 62 are aligned on axis A when needle 62 is retracted into proximal end portion 112 as illustrated, and capsule 152 is aligned on an axis C that is not aligned with axis A.

Figure 7B:
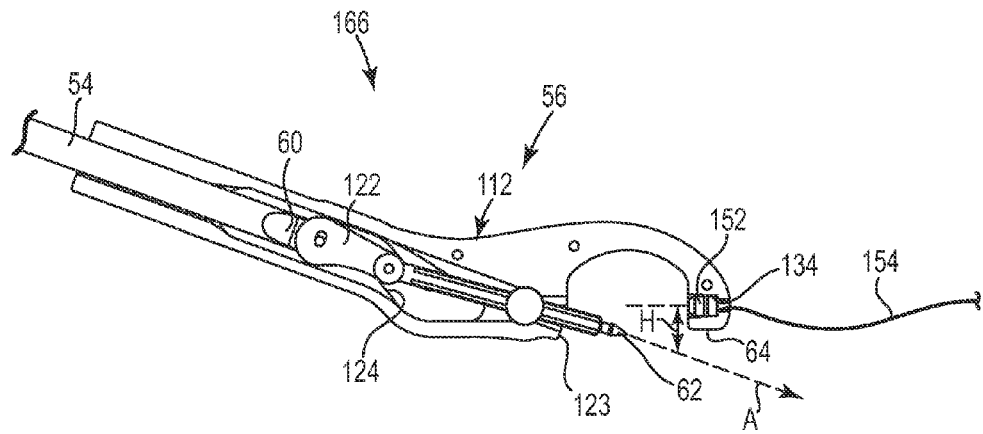
FIG. 7B is a cross-sectional view of the head of the suturing instrument illustrated in FIG. 5 with the needle partially extending from an exit port of the head according to one embodiment.

FIG. 7B is a schematic cross-sectional view of system 166 with needle 62 partially extending from needle exit port 123 after activation of actuator 58 (FIG. 1). Moving rod 60 axially in a distal direction moves needle 62 out of needle exit port 123 in a first direction along axis A. In one embodiment, distal end 64 is radially spaced apart from longitudinal axis A by a distance H, such that the first direction is oriented along axis A, which results in the pathway of needle 62 being offset from cavity 134 by a distance H. A portion of needle 62 extends from needle exit port 123 partway across throat 132, and guide pin 130 is configured to rotate counter-clockwise to allow the movement of link 122 within trace 124 to shunt the leading end 158 of needle 62 away from the first direction oriented along axis A to a second direction aligned with an axis C that extends through cavity 134.

Figure 7C:
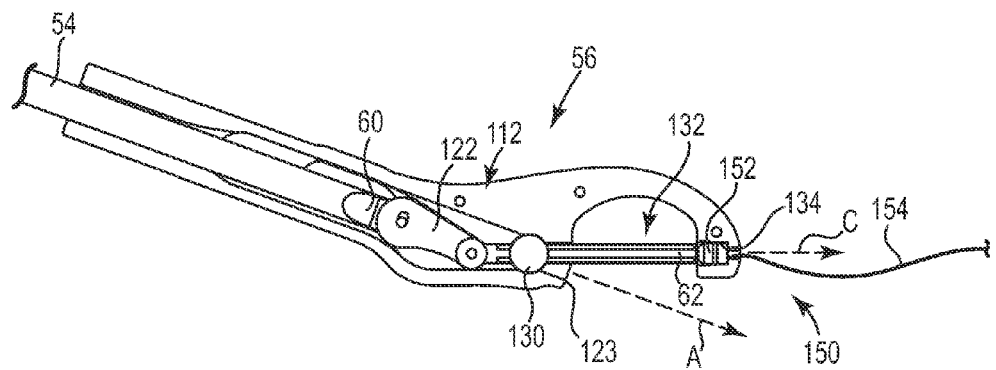
FIG. 7C is a cross-sectional view of the head of the suturing instrument illustrated in FIG. 5 with the needle thrown into the distal end of the head and engaged with the suture assembly illustrated in FIG. 6 according to one embodiment.

FIG. 7C is a schematic cross-sectional view of system 166 including needle 62 shunted away from longitudinal axis A by link 122 and pin 130, moved in a second direction along axis C by rod 60, and engaged with capsule 152. Guide pin 130 has rotated counterclockwise to allow the movement of link 122 within trace 124 to shunt the direction of needle 62 out of alignment with axis A and into alignment with axis C. Additional forward movement of rod 60 will further direct needle 62 across throat 132 and into engagement with capsule 152. As described below, needle 62 is reversible along the paths coincident with axis C and axis A to retract needle 62 and capsule 152 into needle exit port 123.

Figure 7D:
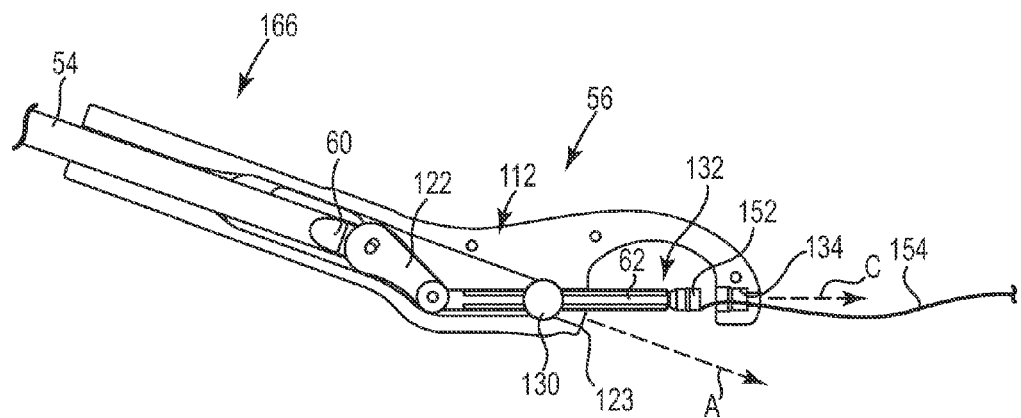
FIGS. 7D-7F are schematic cross-sectional views of the needle of the suturing instrument illustrated in FIG. 1 engaged with the suture assembly and retracting a capsule of the suture assembly back into a proximal end portion of the head according to one embodiment.
Figure 7E:
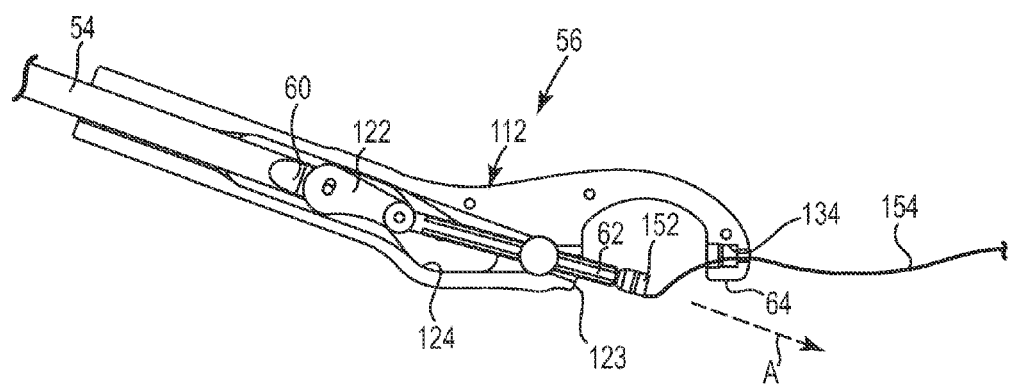
Figure 7F:
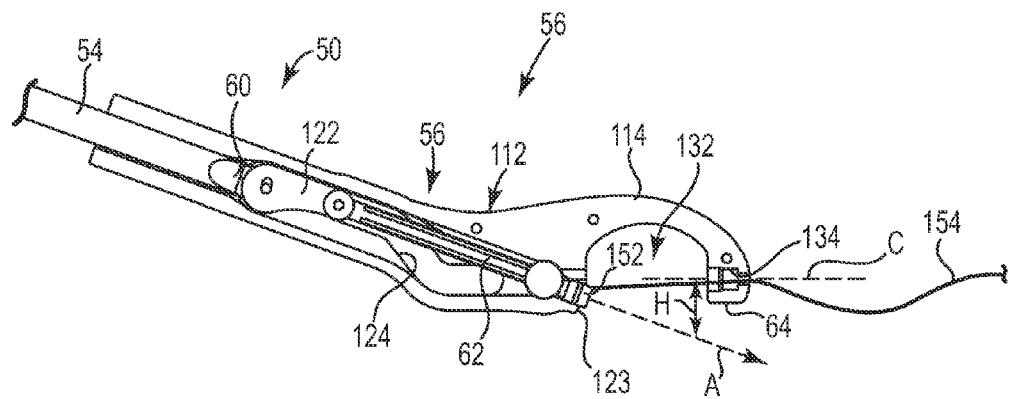

FIGS. 7D-7F are schematic cross-sectional views of needle 62 engaged with capsule 152 and operable to retract and park capsule 152 back in the proximal end portion 112 of head 56.

FIG. 7D is a schematic view of needle 62 engaged with capsule 152 and retracted along axis C a short distance such that capsule 152 is extracted out of cavity 134 and into throat 132. Additional rearward retraction of rod 60 will cause guide pin 130 to rotate clockwise to allow the movement of link 122 within trace 124 to shunt needle 62 off of axis C and into alignment with axis A. Suture 154 trails behind capsule 152 and out of a backside of cavity 134.

FIG. 7E is a schematic view of needle 62 partially retracted into proximal end portion 112 of head 56. Link 122 has moved to a midpoint of trace 124 such that needle 62 and capsule 152 have shunted down into alignment with axis A. Retraction of rod 60 axially into shaft 54 draws needle 62 and capsule 152 into needle exit port 123.

FIG. 7F is a schematic view of needle 62 retracted into head 56 with capsule 152 parked in needle exit port 123. In one embodiment, needle exit port 123 is sized to receive capsule 152 such that port 123 forms a capsule garage 123 into which capsule 152 is parked after extraction from cavity 134. Rod 60 has drawn link 122 into full rearward engagement with trace

124 such that needle 62 is aligned with axis A and retracted into head 56. Capsule 152 is parked inside needle exit port 123 and suture 154 extends across throat 132, which provides the surgeon with guidance and control of the suture line.

In one embodiment, and as described above with reference to FIG. 2, knob 80 is configured to be turned to incrementally retract rod 60 an additional distance into handle 52, which separates needle 62 from capsule 152 that is parked in needle exit port 123. For example, the additional retraction of needle 62 by the rearward motion of rod 60 causes capsule 152 to be pressed against guide pin 130, which shears capsule 152 off of needle 62. Needle 62 is thus disengaged from capsule 152, which leaves capsule 152 parked in needle exit port 123. The removal of instrument 50 from the surgical site gives the surgeon access to head 56 for the extraction of capsule 152 from needle exit port 123. The surgeon thereafter ties and terminates suture 154 as desired.

Embodiments of the suturing device described herein provide a method of suturing tissue useful in many surgical procedures, including the treatment of pelvic organ prolapse. For example, embodiments provide a suturing device suited for the surgical treatment of pelvic organ prolapse that is operable to suture a scaffold or other support to a ligament or other tissue located relative to the pelvic floor. With some surgical procedures it is desirable to apply sutures to the sacrospinous ligament and/or in the arcus tendineus ligament to attach a synthetic scaffold thereto that is configured to support the pelvic floor and reduce or eliminate the undesirable effects of pelvic organ prolapse.

Figure 8:
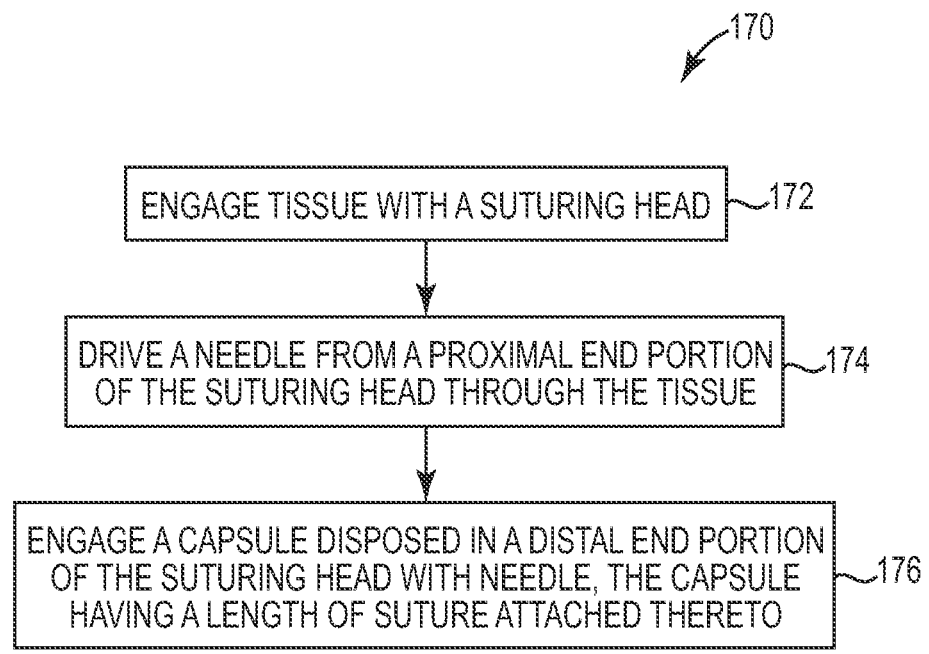
FIG. 8 is a flow diagram of a method of suturing tissue according to one embodiment.

FIG. 8 is a flow diagram 170 of a method of suturing tissue. The method includes engaging tissue with a suturing head at 172. For example, a catheter is placed in the patient's urethra U, along with other recommended, desirable, and preliminary steps in preparation for surgery. The patient is typically placed on an operating table in a lithotomy position with buttocks extending just beyond an edge of the table. With the patient under anesthesia, a vaginal incision (female) or a perineal incision (male) is made by the surgeon. Thereafter, the surgeon would typically palpate the patient to identify a desired landmark, such as the sacrospinous ligament or arcus tendineus ligament or other tissue landmark. The surgeon identifies the landmark, for example with a finger, and subsequently introduces sterile instrument 50 and engages throat 132 (FIG. 5) with the identified landmark.

At 174, the method includes driving a needle from a proximal portion of the suturing head through the tissue. Referencing FIG. 1 as an example, the surgeon activates actuator 58 to drive needle 62 out of proximal end portion 112 of head 56, through tissue, and into the identified ligament.

At 176, the method includes engaging the capsule retained in the distal end of the suturing head with a needle, the capsule including a length of suture attached thereto. For example, the physician drives needle 62 through the desired tissue location with actuator 58 until needle 62 engages with capsule 152. Needle 62 forms a lesion in the tissue, and retracting needle 62 pulls capsule 152 through the lesion with suture 154 following behind. The head 56 is disengaged from the landmark and suturing device is removed from the patient to enable the physician to access and tie the suture.

The above-described methodology may be repeated at another site by inserting a new, second capsule and suture assembly into cavity 134 of head 56 and delivering the new suture assembly 150 to another tissue location of the patient. Upon completion of the procedure, suturing assembly 50 (FIG. 1) is properly disposed of in an approved waste stream of the surgical facility.

Needle 62 is deployed from head 56, and head 56 is compatible with multiple different handle and/or shaft configurations, several of which are described below.

Figure 9A:
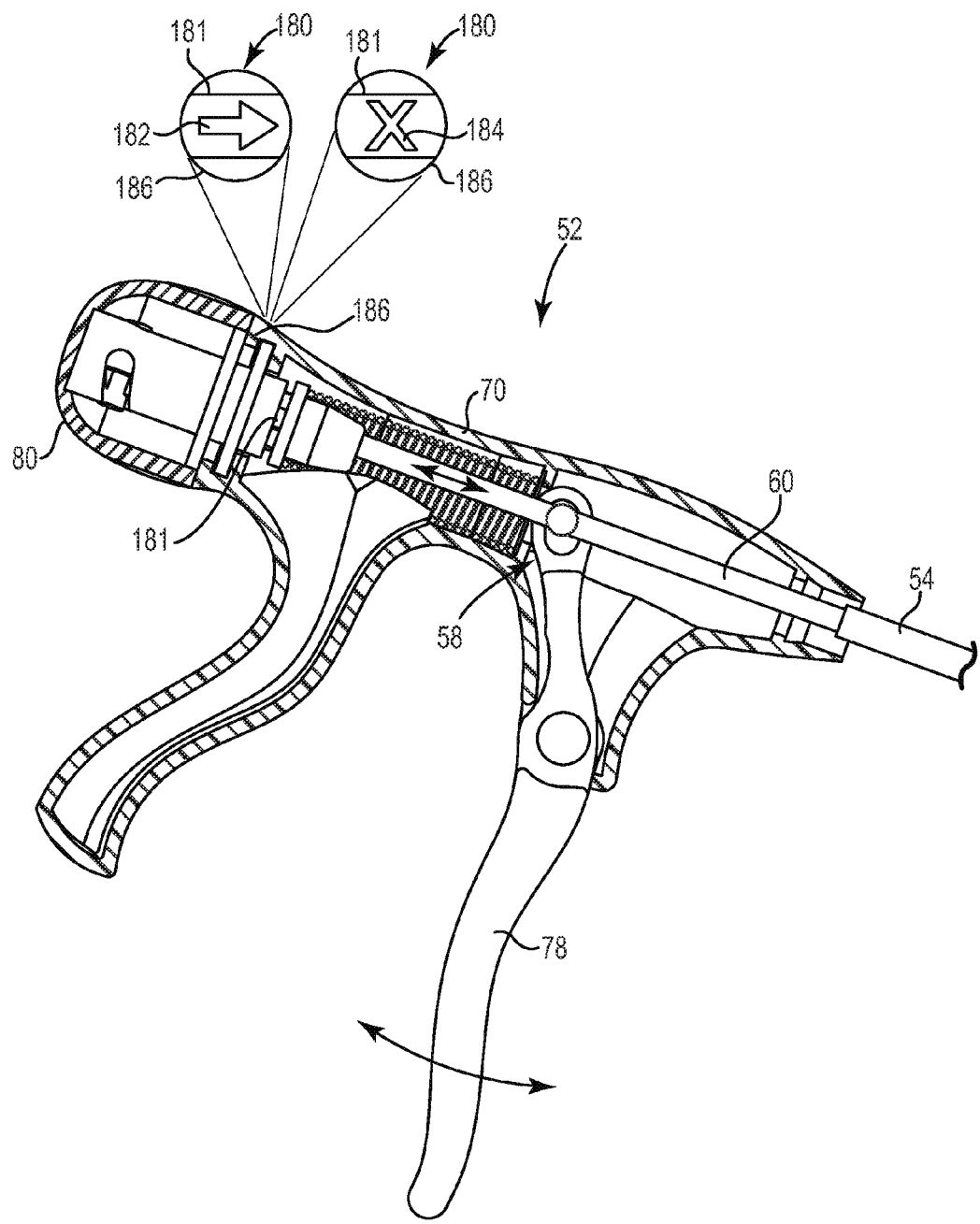
FIG. 9A is a cross-sectional view of another embodiment of a handle configured for use with the suturing instrument illustrated in FIG. 1.

FIG. 9A is a schematic cross-sectional view of handle 52 including a visual indicator 180. Handle 52 is similar to the handle illustrated in FIG. 2 and includes trigger 78 that is configured to move rod 60 axially forward and backward within shaft 54. In one embodiment, visual indicator 180 is formed as a see-through window 186 that enables a user to look through body 70 of handle 52 to discern a positional state of push rod 60.

In one embodiment, visual indicator 180 is configured to indicate a first state in which needle 62 is responsive to actuator 58 and ready to be thrown to engage with capsule 152 (FIG. 7A), and a second state identifying when knob 80 has been turned to disengage capsule 152 from needle 62 (FIG. 7F) and needle 62 is not ready to be thrown to engage with another capsule 152.

For example, as described above, knob 80 is employed (e.g., turned) to further retract rod 60 into handle 52 and disengage capsule 152 from needle 62. When knob 80 has been turned and capsule 152 has been disengaged from needle 62, rod 60 is "captured" by knob 80 and prevented from moving forward when trigger 78 is activated. Returning knob 80 to its initial position enables trigger 78 to fire (or throw) needle 62 into engagement with cavity 134 and capsule 152 within cavity 134.

In one embodiment, a proximal end 181 of rod 60 includes a deployment indicator 182 and a separate retracted indicator 184. Indicator 182 is configured to indicate that rod 60 is ready to be moved axially forward within shaft 54 to push needle 62 out of needle exit port 123. For example, when the deployment indicator 182 is visible within window 186 the user is informed that rod 60 is ready to deploy needle 62 and capture a capsule 152 (the action of which is termed "throwing a suture").

Retracting rod 60, for example by the spring-action described above, returns rod 60 to the retracted position indicated in FIG. 9A. When rod 60 is drawn incrementally further back into handle 52 by turning knob 80, for example to disengage capsule 152 from needle 62 (FIG. 7F), retracted indicator 184 becomes visible within window 186. The presence of retracted indicator 184 within window 186 indicates that needle 62 has been disengaged from capsule 152 and that knob 80 has not been returned to its initial position (and thus, rod 60 is not ready to fire needle 62).

In one embodiment, deployment indicator 182 is provided as a first color and retracted indicator 184 is provided as a second color different from the first color. For example, in one embodiment deployment indicator 182 is green to indicate that needle 62 is ready to be thrown to engage with capsule 152 and retracted indicator 184 is red to indicate that knob 80 has been turned and needle 62 is not in position or ready to be fired toward capsule 152. In another exemplary embodiment, deployment indicator 182 is provided as an arrow to indicate that needle 62 is ready to be thrown to engage with capsule 152 and retracted indicator 184 is provided as an X to indicate that knob 80 has been turned and needle 62 is not in position or ready to be fired toward capsule 152.

Figure 9B:
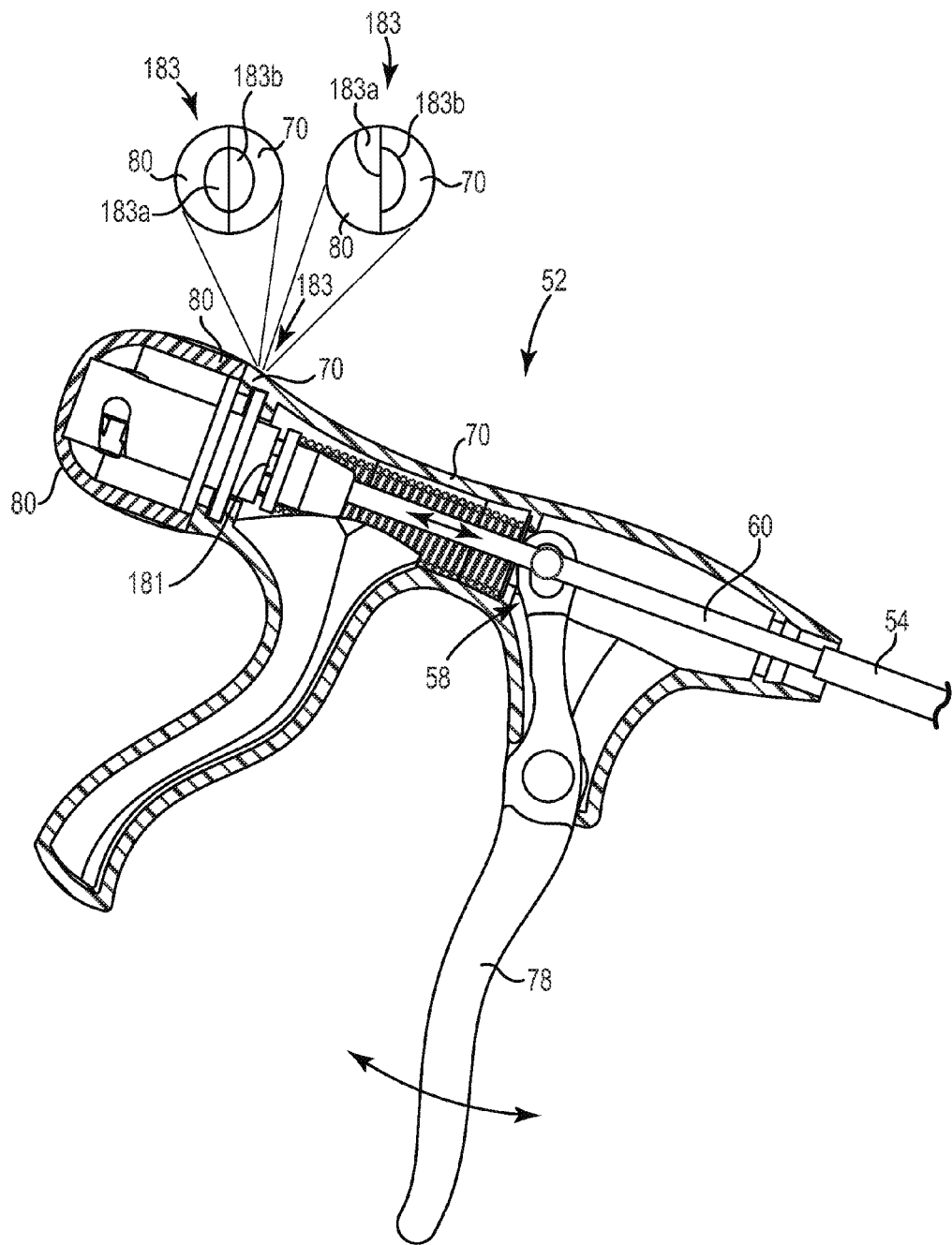
FIG. 9B is a cross-sectional view of another embodiment of a handle configured for use with the suturing instrument illustrated in FIG. 1.

FIG. 9B is a cross-sectional view of another embodiment of an indicator 183 for handle 52. In one embodiment, indicator 183 includes a first 183a indicia located on knob 80 and a second 183b indicia located on body 70 of handle 52. With additional reference to FIGS. 7A-7F, first 183a indicia is aligned with second 183b indicia when rod 60 is in position to fire needle 62 to engage capsule 152, or when knob 80 has been returned to its initial position to ready rod 60 to fire needle 62 to engage capsule 152. For example, first 183a indicia is a semi-circle or a mirror image of second 183b indicia. When first 183a indicia is aligned with second 183b indicia and rod 60 is ready to fire needle 62, the images align as illustrated.

When knob 80 has been turned to retract rod 60 and disengage capsule 152 from needle 62, first 183a indicia is not aligned with second 183b indicia, which indicates to the user that needle 62 is not ready to be fired. For example, the half-oval of first 183a indicia does not aligned with its mirror image of the half-oval of second 183b indicia, as illustrated. However, knob 80 may be turned by the user to return it to its initial position in which rod 60 is in position to fire needle 62 to engage capsule 152, in which case 183a becomes aligned with 183b. Indicator 183 includes color indicators, shapes on handle 52 and knob 80 that mate to indicate alignment of knob 80 with handle 52 (as illustrated), or letters or numbers that indicate alignment and/or non-alignment of knob 80 with handle 52.

Figure 10:
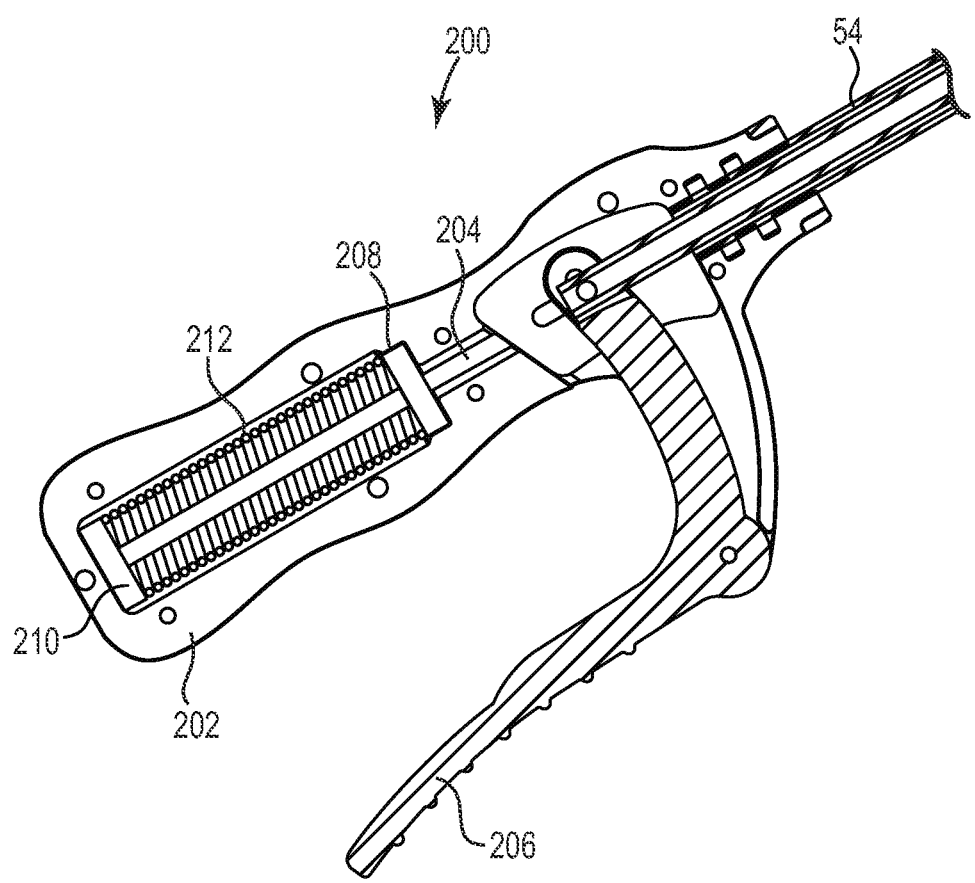
FIG. 10 is a cross-sectional view of another embodiment of a handle configured for use with the suturing instrument illustrated in FIG. 1.

FIG. 10 is a schematic cross-sectional view of another handle 200 configured for use with suturing device 50 illustrated in FIG. 1. Handle is fabricated with materials similar to handle 52 described above.

In one embodiment, handle 200 includes a grip 202 coupled to shaft 54, a rod 204 disposed within shaft 54, and a trigger 206 coupled to rod 204 and configured to displace rod 204 axially within shaft 54. In one embodiment, grip 202 includes a fixed collar 208 and rod 204 includes a base 210 that moves relative to collar 208 when trigger 206 is squeezed. In one embodiment, a biasing member 212 is disposed between collar 208 and base 210. Squeezing trigger 206 draws base 210 toward fixed collar 208, which moves rod 204 in a distal direction and stores energy within biasing member 212. Releasing trigger 206 causes biasing member 212 to force base 210 back in a proximal direction to its neutral state. In this manner, handle 200 provides a bike brake-style handle that enables rod 204 to move forward and back within shaft 54 when trigger 206 is activated.

In one embodiment, handle 200 is provided in a familiar-to-use "bike brake-style" that provides trigger 206 coupled to grip 202 at an angle between 0-10 degrees relative to the axis of shaft 54. In one example of this bike brake-style trigger 206 is substantially parallel to grip 202.

Figure 11:
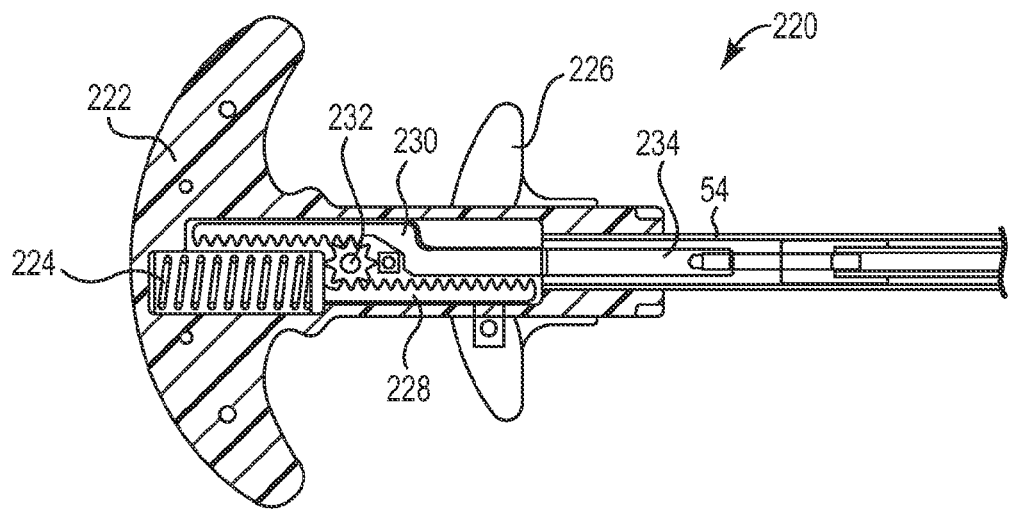
FIG. 11 is a cross-sectional view of another embodiment of a handle configured for use with the suturing instrument illustrated in FIG. 1.

FIG. 11 is a schematic cross-sectional view of another handle 220 configured for use with suturing device 50 illustrated in FIG. 1. In one embodiment, handle 220 includes a proximal handle 222, a biasing member 224 disposed within proximal handle 222, a collar 226, a first geared rack 228 attached to collar 226 and communicating with biasing member 224, a second geared rack 230 disposed within proximal handle 222, and a fixed gear 232 disposed between first geared rack 228 and second geared rack 230.

In one embodiment, proximal handle 222 is curved to accommodate palm of a user, and collar 226 is configured to be engaged by fingers of the user to pull collar 226 toward handle 222. First geared rack 228 is fixed relative to collar 226 and second geared rack 230 is attached to push rod 234. The geared racks 228, 230 move relative to each other by action of gear 230 which is mated between racks 228, 230. When collar 226 is squeezed toward proximal handle 222, gear 232 rotates clockwise and geared rack 228 moves toward proximal handle 222, which compresses biasing member 224. The rotation of gear 232 causes geared rack 230 to translate in the distal direction (e.g., forward, along with handle 222), which pushes rod 234 in a forward direction. Since rod 234 is coupled to needle 62 (FIG. 5), needle 62 is thus moved forward (e.g., "thrown") when collar 226 is squeezed toward the arched proximal handle 222 of handle 220. Biasing member 224 forces collar 226 away from handle 222 when the squeezing force is relaxed, this "reloads" collar 226 to subsequently throw additional sutures. The broad area of proximal handle 222 comfortably distributes the applied force across the hand of the user and collar 226 provides positive engagement with the fingers. These aspects combine to enable the user to direct high levels of force to the push rod 234 in a comfort manner with little effort, which can be advantageous for user's who have smaller hands.

Figure 12:
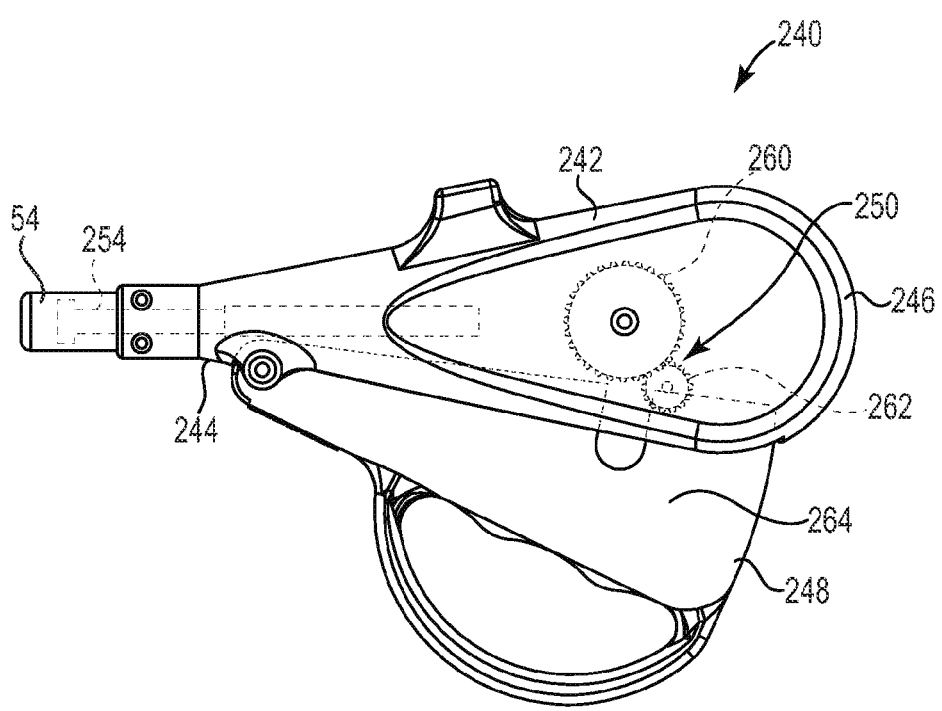
FIG. 12 is a cross-sectional view of another embodiment of a handle configured for use with the suturing instrument illustrated in FIG. 1.

FIG. 12 is a schematic cross-sectional view of another handle 240 configured for use with the suturing device 50 illustrated in FIG. 1. Handle 240 is configured such that squeezing motion delivered laterally relative to shaft 54 results in axial movement of needle 62 from head 56 (FIG. 5).

In one embodiment, handle 240 includes a grip 242 defining a distal end portion 244 opposite a proximal end 246, a squeezable member 248 pinned to the distal end portion 244 of grip 242, and an actuator 250 that is configured to translate the lateral squeezing movement of squeezable member 248 to axial movement of a rod 254 disposed within shaft 54. In one exemplary embodiment, actuator 250 includes a first gear 260 disposed within grip 242 and mated to a second gear 262, and squeezable member 248 includes a geared rack 264 that is engaged with the second gear 262. Rod 254 is coupled with first gear 260. When squeezable member 248 is compressed laterally into grip 242, geared rack 264 moves laterally and rotates gear 262 in a counter-clockwise direction, which causes gear 260 to rotate in a clockwise direction. The rotation of gear 260 is translated to axial movement of rod 254 (and thus needle 62). In another exemplary embodiment, gear 260 is attached to a pair of cables that are spaced 180 degrees apart on round gear 260. The cables extend to a forward gear or pulley located within head 56 (FIG. 5). The cables are balanced in a pulley arrangement such that rotation of gear 260 clockwise tensions the upper cable, which rotates the forward gear clockwise to tension the lower cable. Thus, the cables replace the push/pull function of rod 254.

In one embodiment, grip 242 is fabricated from plastic similar to the handles for instrument 50 described above and is molded to include an ergonomic tear-drop shape.

Figure 13:
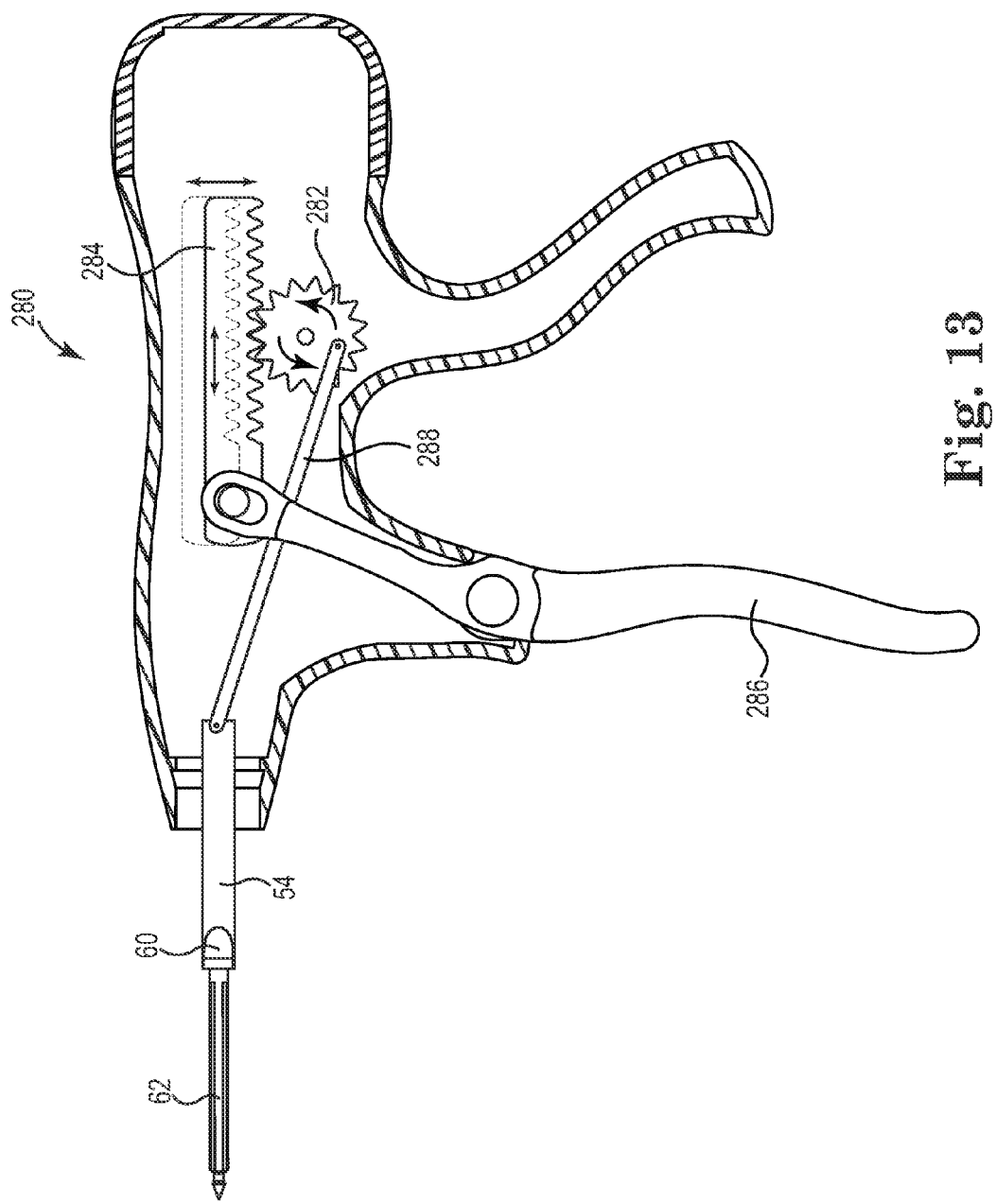
FIG. 13 is a cross-sectional view of another embodiment of a handle configured for use with the suturing instrument illustrated in FIG. 1.

FIG. 13 is a schematic view of another handle 280 configured for use with suturing device 50 illustrated in FIG. 1. Handle 280 is similar to handle 52 (FIG. 1) and includes a trigger 286 that is configured to eject needle 62 from head 56 with a first squeeze of trigger 286 and retract needle 62 into head 56 with a subsequent squeeze of trigger 286.

In one embodiment, handle 280 includes a uni-directional gear 282 coupled to a rack 284 that is provided with two degrees of freedom. For example, trigger 286 is pinned to rack 284, and a link 288 is pinned between gear 282 and rod 60. Gear 282 is configured to rotate in only one direction (i.e., uni-directionally), which in this embodiment is counter-clockwise. In an initial position, link 288 is positioned at the 3 o'clock position of gear 282 (e.g., at the top), and squeezing trigger 286 rotates gear 282 counter-clockwise to the 9 o'clock position, which displaces link 288 distally forward to push rod 60 forward. Releasing trigger 286 causes rack 284 to lift and skip over the teeth in gear 282 (i.e., without gear 282 and rack 284 meshing), leaving link 288 at the 9 o'clock position. Thus, rack 284 has at least two degrees of freedom: laterally left and right as oriented in FIG. 13 and up/down to disengage from gear 282. In this manner, rack 284 is retracted proximally backwards relative to gear 282 without rotating gear 282. A second squeeze of trigger 286 again draws rack 284 forward and into engagement with gear 282, rotating gear 282 counter-clockwise, which draws link 288 rearward from the 9 o'clock position back and up to the 3 o'clock position to retract push rod 60 within shaft 54. In this manner, handle 280 provides a double action trigger 286 configured to throw a suture by moving needle 62 forward with a first pull of trigger to 86 and retract needle with a second pull of trigger 286.

The above described handles enable a surgeon to accurately and securely place a suture in tissue. In one embodiment, shaft 54 is provided as a rigid shaft. However, the surgeon may desire to adjust the location of head 56 as a suture is thrown, or as subsequent sutures are placed. Instrument 50 provides for positional flexibility of head 56, for example via flexible end section 98 of shaft 54 (FIG. 3). Additional embodiments of flexible shafts that provide the surgeon with flexibility in placing sutures are described below.

Figure 14:
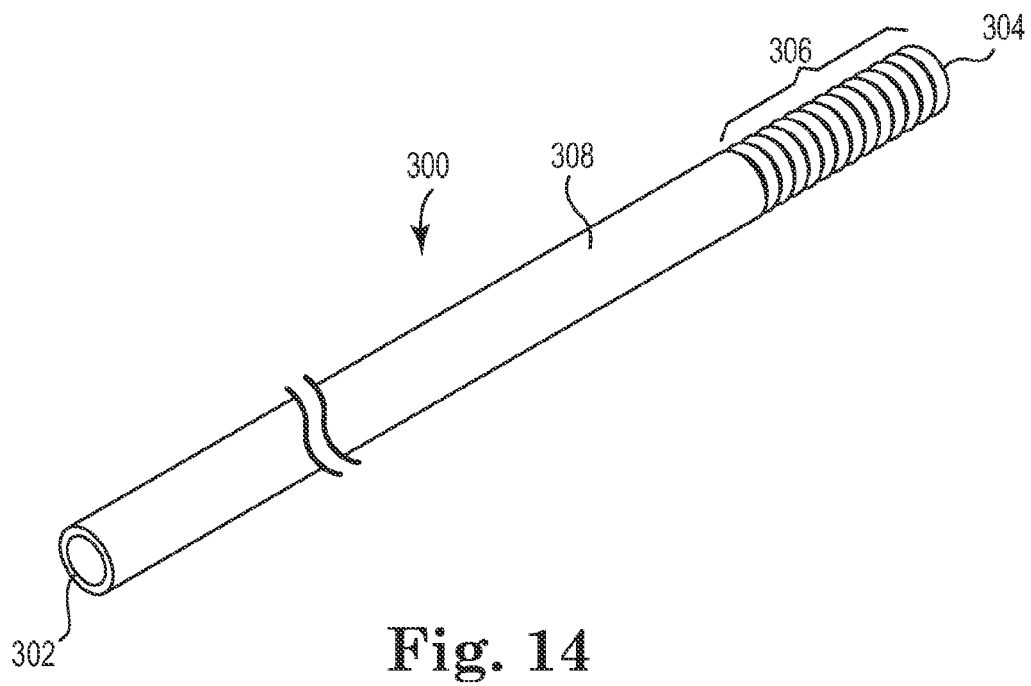
FIG. 14 is a perspective view of another embodiment of a shaft configured for use with the suturing instrument illustrated in FIG. 1.

FIG. 14 is a perspective view of another embodiment of a shaft 300 configured for use with suturing instrument 50 illustrated in FIG. 1. Shaft 300 includes a proximal end 302 that is attachable to a handle (such as handle 52 in FIG. 1) and a distal end 304 that couples with a suture throwing head (such as head 56 in FIG. 1). In one embodiment, a distal end portion 306 of shaft 300 includes a corrugated section that provides distal end portion 306 with lateral flexibility relative to section 308. In one embodiment, shaft 300 is fabricated from stainless steel, and distal portion 306 is provided with an accordion-style corrugated structure that provides lateral flexibility for distal end 304 of shaft 300. Suitable metals for shaft 300 include aluminum, steel including stainless steel, highly malleable metal such as copper, or other such suitable metals.

Figure 15:
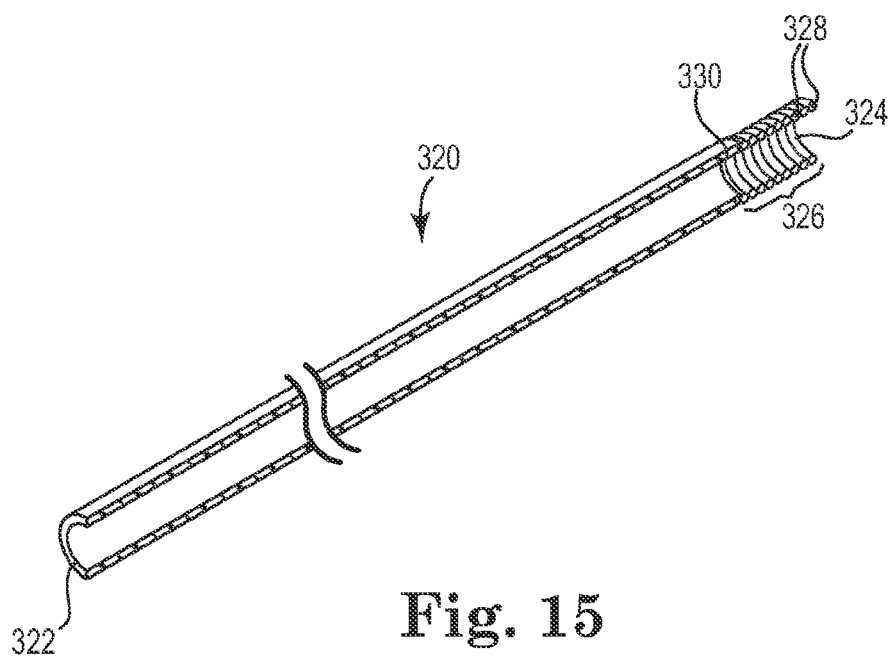
FIG. 15 is a cross-sectional view of another embodiment of a shaft configured for use with the suturing instrument illustrated in FIG. 1.

FIG. 15 is a perspective view of another embodiment of a shaft 320 configured for use with suturing instrument 50 illustrated in FIG. 1. Shaft 320 includes a proximal end 322 that is attachable to a handle (such as handle 52 in FIG. 1) opposite a distal end 324 that couples with a suture throwing head (such as head 56 in FIG. 1), and a distal end portion 326 including one or more flexible coils 328. In one embodiment, coils 328 are attached to an end portion 330 of shaft 320, for example by soldering or welding. In another embodiment, coils 328 are disposed over a rigid end portion of shaft 320 and crimped in place. That is to say, in one embodiment coils 328 are integrally formed with shaft 320, and in a separate embodiment coils 328 are provided separate from shaft 320 and subsequently attached thereto. In any regard, distal end portion 326 of shaft 320 is provided with flexibility in the lateral direction that enables the surgeon to move head 56 laterally relative to the longitudinal axis of shaft 320. In one embodiment coils 328 are formed from copper and attached to end portion 330 of a stainless steel shaft 320.

Figure 16:
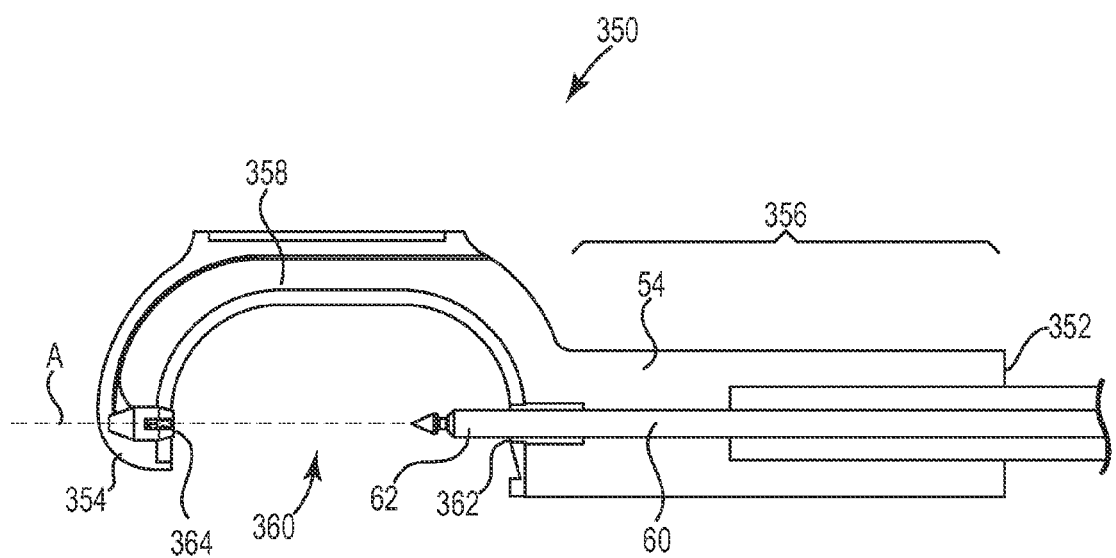
FIG. 16 is a cross-sectional view of another embodiment of a head configured for use with the suturing instrument illustrated in FIG. 1.

FIG. 16 is a cross-sectional view of another head 350 configured for use with suturing assembly 50 illustrated in FIG. 1. Head 350 is coupled to shaft 54 such that rod 60 extends through a portion of head 350 to couple with needle 62.

In one embodiment, head 350 includes a proximal end 352 opposite a distal end 354, a proximal end portion 356 extending from proximal end 352, and a neck 358 that extends between proximal end portion 356 and distal end 354. In one embodiment, a throat 360 is formed between proximal end portion 356 and distal end 354, where proximal end portion 356 defines a needle exit port 362 through which needle 62 moves.

In one embodiment, head 350 is provided as a linear head having a distal end 354 that defines a cavity 364 aligned with the major longitudinal axis A of the suturing device. Cavity 364 is sized and configured to retain capsule 152 of suturing assembly 150 (FIG. 7). In one embodiment, needle 62 is provided as a substantially straight needle that is aligned on axis A of shaft 54 when stowed (e.g., stored or parked) within proximal portion 356 of head 350. Needle 62 moves longitudinally out of needle exit port 362 along a substantially linear (straight) line and traverses throat 360 by traveling along axis A. As described above, needle 62 is configured to engage capsule 152, remove capsule 152 from cavity 364, and pull capsule 152 (and suture attached to capsule 152) proximally back across throat 360 to suture tissue engaged in throat 360.

Head 56 (FIG. 5) provides an offset distal end 64 and head 350 alternatively provides a linear arrangement between distal end portion 356 and distal end 354. Rod 60 is rigidly coupled to needle 62, although it is acceptable to have a link coupled between rod 60 and needle 62, as described above, where the link translates within a channel to move needle 62 along axis A and into engagement with capsule 152 (FIG. 7) that is retained within cavity 364. In one preferred embodiment, rod 60 is rigidly coupled with needle 62 and configured to drive needle 62 directly across throat 360 and into engagement with a capsule/suture assembly placed in cavity 364. Other mechanisms for linearly delivering needle 62 from proximal end portion 356 of head 350 are also acceptable.

Figure 17:
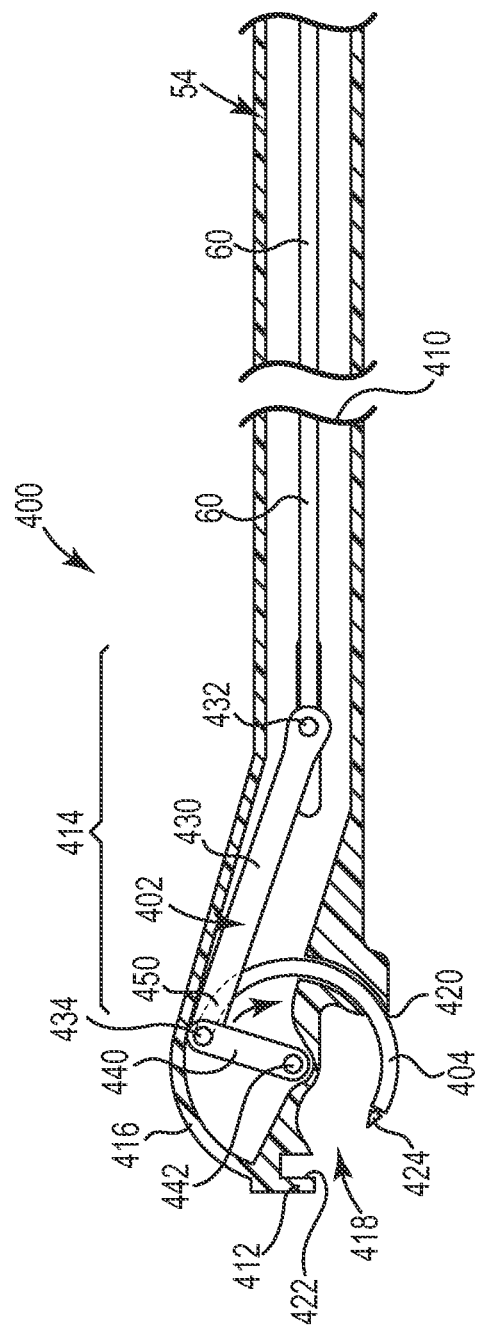
FIG. 17 is a cross-sectional view of another embodiment of a head configured for use with the suturing instrument illustrated in FIG. 1.

FIG. 17 is a cross-sectional view of another head 400 configured for use with suturing assembly 50 illustrated in FIG. 1. Head 400 is configured to be coupled to shaft 54 such that rod 60 extends through a portion of head 400 to couple with a linkage 402 that communicates with a curved needle 404.

Head 400 includes a proximal end 410 opposite a distal end 412, a proximal end portion 414 extending from proximal end 410, and a neck 416 that extends between proximal end portion 414 and distal end 412. In one embodiment, a throat 418 is formed between proximal end portion 414 and distal end 412, where proximal end portion 414 defines a needle exit port 420 through which curved needle 404 exits proximal end portion 414.

In one embodiment, distal end 412 defines a cavity 422 that is sized and configured to retain capsule 152 of suturing assembly 150 (FIG. 7). Suture 154 (FIG. 7) of suture assembly 150 is directed over distal end 412 and proximal end portion 414 for management by the surgeon near the handle located proximal of the instrument. Curved needle 404 moves clockwise in this embodiment out of needle exit port 420 and includes a leading end 424 that is configured to engage with capsule 152, remove capsule 152 from cavity 422, and pull capsule 152 (and suture attached to capsule 152) counterclockwise back across throat 418 to suture tissue engaged in throat 418.

In one exemplary embodiment, linkage 402 includes a first link 430 and a second link 440, where first link 430 includes a pin 432 coupled to rod 60 and a second pin 434 coupled to second link 440. Second link 440 has a pin 442 that defines a pivot point about which link 440 and needle 404 rotates. In one embodiment, a trailing end 450 of curved needle 404 is coupled to a juncture of first link 430 and second link 440 by pin 434.

Rod 60 is retractable, for example by actuator 58 illustrated in FIG. 1. Movement of rod 60 toward distal end 412 of head 400 moves first link 430 in a forward direction, causing second link 440 to rotate about pivot point 442. In particular, pin 434 in second link 440 moves in a counter-clockwise motion relative to pivot point 442. The counter-clockwise motion of pin 434 draws curved needle 404 in a counter-clockwise retracting motion that opens throat 418. Conversely, rod 60 is movable backwards in a proximal direction that draws pin 432 and link 430 rearward, which rotates pin 434 clockwise. Clockwise rotation of pin 434 connected between link 430 and link 440 causes curved needle 404 to move in a clockwise direction across throat 418 and into cavity 422. In this manner, linkage 402 moves curved needle 404 out of needle exit port 420 and away from proximal end portion 414, across throat 418, and into cavity 422 formed in distal end 412 of head 400.

Head 400 thus provides a reversed curved needle suture thrower that is configured to move curved needle 404 away from proximal end portion 414 in an arc, across throat 418, and into engagement with capsule 152 (FIG. 7) retained within cavity 422. Movement of rod 60 as described above retracts capsule from cavity 422 and pulls the capsule back into needle exit port 420.

A suturing system provides a suturing instrument having a needle housed in a proximal end portion of a head, where the needle is movable longitudinally out of the proximal end portion of the head through tissue to subsequently grasp a cap attached to suture. The needle retracts after engaging the cap and pulls the suture through the lesion formed by the needle in the tissue to efficiently throw and retrieve suture.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A suturing assembly configured to pull a capsule attached to a suture through tissue, the suturing assembly comprising:
    a shaft aligned on a longitudinal axis of the suturing assembly; and
    a head coupled to the shaft, the head comprising:
        a proximal portion housing a needle that is movable through a needle exit port, where the proximal portion of the head and the needle exit port are both aligned on the longitudinal axis, and
        a distal end spaced apart from the proximal portion by a throat, where a proximal side of the distal end of the head defines a cavity adapted to receive the capsule and a distal side of the distal end of the head defines a slot adapted to allow the suture to pass through the distal end of the head and into the cavity;
    wherein the capsule is provided with a channel extending from a leading truncated end of the capsule to a trailing end of the capsule, and the channel in the capsule includes a flange formed in a wall of the channel;
    wherein the needle is adapted to be shunted away from the longitudinal axis of the suturing assembly and across the throat for engagement with the flange formed in the wall of the channel of the capsule.

2. The suturing assembly of claim 1, wherein the cavity is aligned on a second axis that is non-parallel with the longitudinal axis.

3. The suturing assembly of claim 1, wherein the cavity is offset radially off of the longitudinal axis.

4. The suturing assembly of claim 1, wherein the needle is adapted to be shunted from the needle exit port to the cavity formed in the distal end of the head.

5. The suturing assembly of claim 1, further comprising:
    a handle comprising an actuator, the handle attached to a proximal end of the shaft and the actuator including a trigger coupled to a rod disposed in the shaft, the rod extending between the handle and the needle.

6. The suturing assembly of claim 5, wherein the handle comprises a knob coupled to a proximal end portion of the handle, the knob, when turned, is configured to retract the rod proximally.

7. The suturing assembly of claim 1, wherein the shaft comprises a rigid shaft.

8. The suturing assembly of claim 1, wherein the distal side of the distal end of the head defines a distal end of the suturing assembly.

9. A suturing assembly configured to pull a capsule attached to a suture through tissue, the suturing assembly comprising:
    a shaft aligned on a longitudinal axis of the suturing assembly; and
    a head coupled to the shaft, the head comprising:
        a proximal portion housing a needle that is movable through a needle exit port formed in the proximal portion of the head, where the proximal portion of the head and the needle exit port are both aligned on the longitudinal axis, and
        a distal end spaced apart from the proximal portion by a throat;
    wherein the distal end of the head defines an aperture that is offset radially off of the longitudinal axis, the aperture adapted to retain the capsule;
    wherein the needle is adapted to exit the needle exit port and be shunted into the aperture formed in the distal end of the head for subsequent engagement with the capsule.

10. The suturing assembly of claim 9, wherein the needle is adapted to retrieve the capsule into the needle exit port.

* * * * *